United States Patent [19]

Ninomiya et al.

[11] Patent Number: 5,138,158
[45] Date of Patent: Aug. 11, 1992

[54] SURFACE ANALYSIS METHOD AND APPARATUS

[75] Inventors: Ken Ninomiya, Hachioji; Shigeru Nishimatsu, Kokubunji, both of Japan

[73] Assignee: Hitachi, Ltd., Tokyo, Japan

[21] Appl. No.: 378,400

[22] Filed: Jul. 11, 1989

[30] Foreign Application Priority Data

Jul. 15, 1988 [JP] Japan ................. 63-175023

[51] Int. Cl.$^5$ .............................. G01N 23/227
[52] U.S. Cl. .................... 250/305; 250/306
[58] Field of Search ........... 250/305, 304, 306, 307, 250/309, 310, 311, 491.1, 492.1, 492.2, 492.21, 492.23, 492.3

[56] References Cited

U.S. PATENT DOCUMENTS

| | | | |
|---|---|---|---|
| 3,567,928 | 3/1971 | Davies et al. | 250/305 |
| 3,617,741 | 11/1971 | Siegbahn et al. | 250/305 |
| 3,772,522 | 11/1973 | Hammond et al. | 250/305 |
| 3,783,280 | 1/1974 | Watson | 250/305 |
| 4,382,181 | 5/1983 | Wang | 250/305 |
| 4,680,467 | 7/1987 | Bryson, III et al. | 250/305 |

Primary Examiner—Jack I. Berman
Assistant Examiner—Kiet T. Nguyen
Attorney, Agent, or Firm—Antonelli, Terry, Stout & Kraus

[57] ABSTRACT

Described is a surface analysis method for analyzing energy of particles such as photoelectrons which are emitted from a sample surface by the irradiation of light with wavelengths ranging from the soft x-ray region to the vacuum ultraviolet region using an optical system including a reflective optical element to the sample surface so as to obtain chemical state information about the sample surface, wherein the beam diameter of the light on the sample surface is reduced to 1 μm or less in terms of full width at half maximum of the beam intensity profile on the sample surface so that the chemical state information about the sample surface can be obtained with high sensitivity and high resolution, and an apparatus for implementing this method.

52 Claims, 8 Drawing Sheets

FIG. I
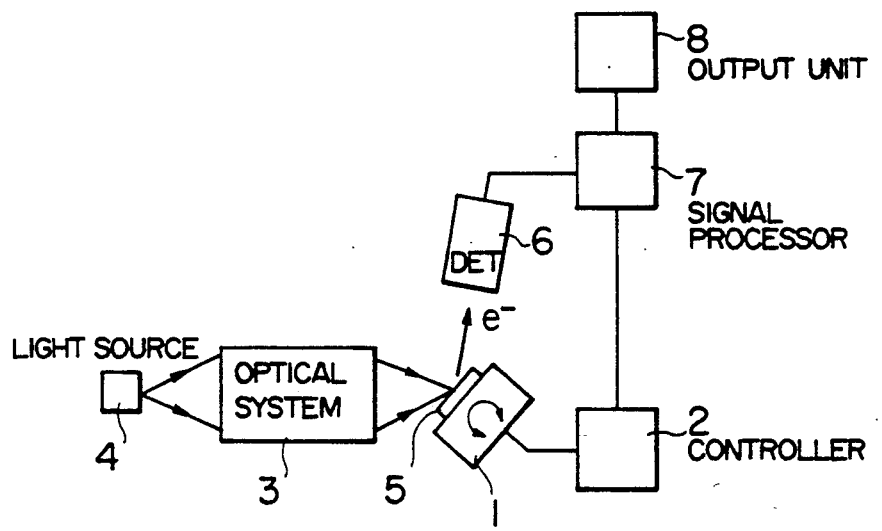
FIG. 2
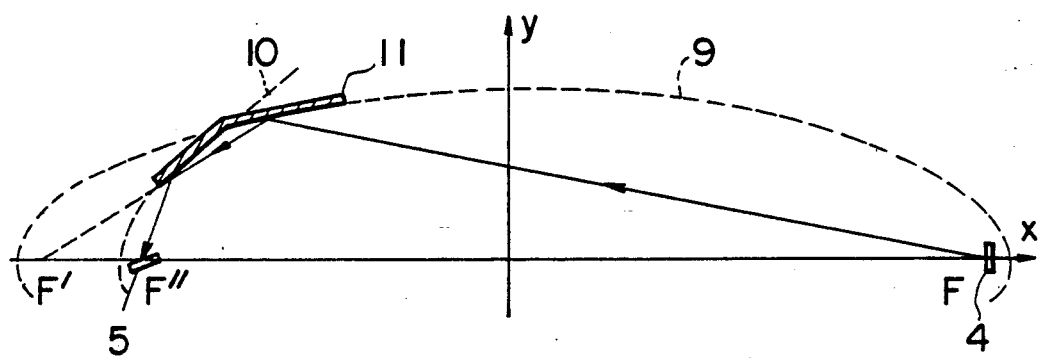

SURFACE ANALYSIS METHOD AND APPARATUS

BACKGROUND OF THE INVENTION

This invention relates to an improvement of a surface analysis method and particularly to a surface analysis method and apparatus suitable for chemical state analysis of small areas on the sample surface to be analyzed.

The development in small surface area analysis is remarkable, and this small area analysis and its technology are generally called "micro-characterization".

The information to be obtained from the small surface area includes the geometrical shape and structure of the surface and the, nearby surface region (hereinafter called the surface), the atomic species, composition and chemical bonds of these atoms within the region, and so on. In addition, the analysis must be non-destructive.

Of the above-given information, the geometrical shape of the surface can now be measured by an STM (scanning tunnelling microscope) and a high resolution SEM (scanning electron microscope). At the present time, the lateral resolution with which the shape is measured is close to 1 Å.

On the other hand, the lateral resolution in analyzing the chemical state such as atomic species and chemical bonds (that is, the extent of the small surface area from which the atomic species and chemical bonds can be identified) is now several tens of $\mu$m which is far poorer as compared with that in measuring the shape.

However, high lateral resolution in analyzing the chemical state seems to be required in the future for the following reasons. For example, the residues on semiconductor circuit devices after surface treatment will remarkably deteriorate the device characteristics. In order to analyze and identify the residues on the actual sample surface, it is necessary to increase the lateral resolution to the minimum pattern size of the devices. When the device pattern size of 0.3 to 0.1 $\mu$m is considered to be achieved in the future, the lateral resolution of 0.1 $\mu$m or less will be required in small area analysis.

Moreover, the actual surface has many defects such as steps. The deposition of materials and chemical reaction such as catalytic reaction on the surface will not advance uniformly due to the presence of the defects. This non-uniformity seems to be in the order of 0.1 to several $\mu$m from the observation of grain boundary (Katsumichi Yagi, et al., Oyo-butsuri, 55, 1036-1050 (1986)). From the standpoint of analyzing the nonuniform phenomena, the resolution of 1 $\mu$m or less will also be required.

In the analysis of single protein molecules which is requested in the biology and biological engineering, the lateral resolution of 0.01 $\mu$m or less is necessary because the protein molecule size is several tens of Å.

The following methods have been proposed for improving the lateral resolution in the surface analysis for obtaining chemical state information.

One of the methods is focusing soft x-rays by a single crystal surface with a curvature in XPS (X-ray photoelectron spectroscopy) (F. J. Grunthaner, MRS Bulletin 30, 60-64 (1987)). In this method, however, the aberration of the optical system is very large, so the beam is limited to about 120 $\mu$m$\phi$. Therefore, the size of the area to be analyzed is 120 $\mu$m$\phi$, so that the lateral resolution of 1 $\mu$m or less cannot be achieved by the method.

Another method for improving the lateral resolution is to generate a strong magnetic field near the sample surface, and catch the photoelectrons emitted from the sample surface by using electron cyclotron motion. The drawback of this method is the fact that the lateral resolution is determined by the Larmor radius $r_b$ of the photoelectron:

$$r_b = v_p m/(eB) \qquad (1)$$

where $v_p$, m, e, and B are the velocity component of photoelectron measured perpendicular to the magnetic field, the mass of electron, the charge of electron, and the magnetic flux density near the sample surface, respectively. Assuming that the photoelectron is emitted with a kinetic energy E at an angle $\theta$ (which is measured from the magnetic field direction) eq. (1) is rewritten in terms of E and $\theta$ as $$r_b = \sqrt{2Em} \sin \theta /(eB) \qquad (2)$$

The lateral resolution by this method is actually determined by 4 $r_b$. As an example, substituting E=10 eV B=20T, $\theta$=90° into eq. (2) will yield 4 $r_b$=2.1 $\mu$m. Thus, the lateral resolution in this method is normally on the order of $\mu$m.

In order to achieve a higher resolution, the angle $\theta$ should be small as is indicated from eq. (2). This means that only a small fraction of the photoelectrons emitted from the sample surface can be utilized in the surface analysis. For example, considering a photoemission differential cross section (R. F. Reilman et al., J. Elect. Spectrosc. Relat. Phenom. 8, 389-394 (1976)), the utilization efficiency of photoelectrons is 1% or less when the lateral revolution is set to 0.06 $\mu$m (4 $r_b$). In addition, the utilization efficiency is more decreased with further increasing lateral resolution. Therefore, this method has a serious disadvantage that photoelectrons can hardly be observed although they are emitted from the sample surface. Moreover, since the lateral resolution depends on kinetic energy E (eq. (2)), the photoelectron kinetic energy cannot be analyzed with a constant lateral resolution.

There is another method that an x-ray is focused by use of a Fresnel zone plate (Japanese Patent Laid-Open Number 265555/1987). This method, however, has a low utilization efficiency of the x-ray. For example, even for the most intense first-order diffraction, the theoretical value of the efficiency is about 10%, while the measured value is about 5%.

An abundant x-ray flux is required for analyzing a small surface area in order to obtain a large detection signal intensity. This is because the number of atoms and molecules in the area is very small. Focusing an x-ray only by the zone plate brings about low signal intensity which is a serious problem of the analysis.

As described above, the conventional methods have a disadvantage of low lateral resolution or low signal intensity. Therefore, it is impossible to obtain chemical state information with lateral resolution of 1 $\mu$m or less.

SUMMARY OF THE INVENTION

It is an object of this invention to provide a surface analysis method and apparatus capable of obtaining chemical state information such as atomic species and chemical bonds with a lateral resolution of 1 $\mu$m or less and also a large signal intensity.

In order to achieve the above object, light in a soft x-ray region to a vacuum ultraviolet region is focused on a sample surface by use of an optical system. Then, the kinetic energy of electrons emitted from the light-irradiated sample surface is analyzed so that chemical state information on the sample surface can be obtained.

The optical system used here is different from that using Bragg reflection on a single crystal surface or that using only the zone plate. It mainly uses reflective optics with small aberrations and a high utilization efficiency of the light.

By employing this optical system, it is possible to focus the light ranging from the soft x-ray region to the vacuum ultraviolet region within a small area of 1 $\mu m\phi$ or less, and thus to analyze the energy of photoelectrons from the small area with a large signal intensity and a high resolution.

In order to analyze the small area, it is necessary to either reduce a probe beam diameter or limit the field of a detector with a non-focused probe beam. When the latter method is employed, there is a possibility that the signal intensity will be reduced or little information will be obtained, as mentioned in the previous section. Thus, the present invention employs a focused probe beam.

The possible probe beams are a charged particle beam (electron an beam or an ion beam) and a light beam. When a charged particle beam is used as a probe beam, it is necessary to give the charged particles kinetic energy of at least 1 keV or more in order to focus them to about 0.01 $\mu m$ diameter area (Takashi Tanaka et al., "Oyo-butsuri" 55, 1153–1156 (1986), and R. Levi-Setti et al. Appl. Surf. Sci. 26, 249–264 (1986)).

It is preferable for analyzing the chemical state of the surface that the energy of the particle beam is about the same as the interaction energy between the atoms and molecules composing the surface region, and the incoming charged particles (for example, several to several hundreds of eV considering excitation or ionization). Energy exceeding this amount will result in a low interaction cross section, thus bringing about a decrease in signal intensity. This further leads to physical sputtering of the sample surface and temperature rise thereof, which does not satisfy the non-destructive analysis. For example, assuming that $10^9$ electrons ($1.6\times10^{-1}$ Å) of 2 keV impinge on a 1-$\mu m$ diameter area in a unit time, the sample surface temperature will rise to 1042K. (Herman Winick and S. Doniach ed., "Synchrotron Radiation Research" (Plenum Press. New York. 1982) page 475). Moreover, it is known that electron beams having kinetic energy of 3 to 7 keV cause the desorption of adsorbed atoms and molecules from the sample surface (electron simulated desorption). The diameter of the charged particle beam can easily be reduced, but this beam makes changes and damages to the sample surface because of its high kinetic energy.

On the other hand, use of light as a probe beam can avoid the high energy problem as will be described later. When the diameter of the probe light beam is set to 0.01 $\mu m$ (as in the above description), the possible wavelength of the light to be used is 0.01 $\mu m$ or less, that is, light in a soft x-ray region should be used (if the beam diameter is about 0.1 $\mu m$, light in a vacuum ultraviolet region can also be used). The energy of the light with wavelength of 0.01 $\mu m$ is around 120 eV, which is much smaller than the energy ($>1$ keV) necessary for focusing the charged particle beams in the same region. Thus, the damage to the sample is small. In addition, since the light beam provides a larger excitation and ionization cross section than the charged particle beam (Herman Winick and S. Doniach ed., "Synchrotron Radiation Research" as given previously), the increase in the interaction cross section can also be expected when light is used. For these reasons, the present invention employs a focused light beam with wavelengths ranging from a soft x-ray region to a vacuum ultraviolet region as a probe beam.

When this invention is applied to the semiconductor device production process, the elements to be analyzed will be a few different elements such as Si, O, C and Al. In a different field of application, other elements are considered to be analyzed. Thus, the method to be used must be capable of analyzing all elements and their chemical bonds. Judging from possible light wavelength and this requirement, the most desirable analysis method is UPS (ultraviolet photoelectron spectroscopy) or XPS (x-ray photoelectron spectroscopy). In UPS or XPS, the vacuum ultraviolet light or the soft x-ray irradiates the sample surface and the photoelectrons emitted from the surface are observed. By analyzing the kinetic energy of these photoelectrons, it is possible to identify atomic species and their chemical bonds in the surface region. In conclusion, this invention employs light ranging from a soft x-ray region to a vacuum ultraviolet region which is focused on the sample surface as a probe beam, and the kinetic energy of photoelectrons emitted from the surface is analyzed.

Finally, methods for focusing the light will be mentioned. The conventional apparatus which uses a focused x-ray to analyze the sample surface employs a crystal for focusing the x-ray (for example, see Japanese Patent Laid-Open No. 179645/1987). However, this invention utilizes an optical system which is chiefly constructed by reflective optics utilizing total reflection. Use of this optical system is able to focus x-ray onto a very small surface area with small aberrations.

BRIEF DESCRIPTION OF THE DRAWINGS

FIG. 1 shows an arrangement of one embodiment of this invention.

FIGS. 2 to 6 are schematic diagrams of examples of the optical systems used in this invention.

DESCRIPTION OF THE PREFERRED EMBODIMENTS

Figure 3:
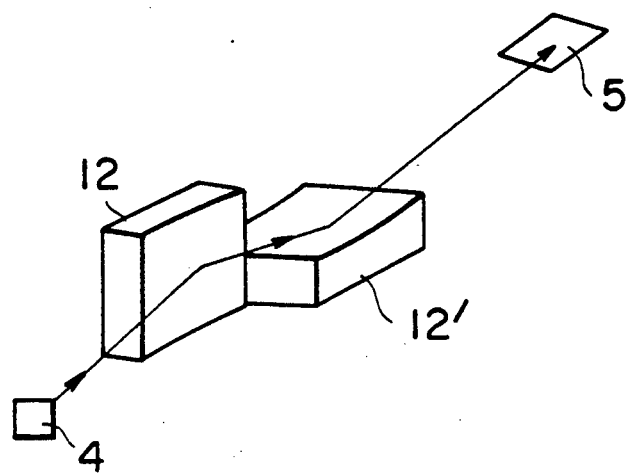

Embodiments of this invention will hereinafter be described with reference to the accompanying drawings.

EMBODIMENT 1

FIG. 1 shows one embodiment of this invention. Referring to FIG. 1, a light source 4 emits light of wavelengths ranging from a vacuum ultraviolet region to a soft x-ray region (about from 6 to 2000 eV), which is focused by optical system 3 onto sample 5. Optical system 3 is one using a reflective optical element which will be described later or its combination. When the sample is irradiated by the light, photoelectrons are emitted from the sample surface. Then, their kinetic energies are analyzed by detector 6. Sample table 1 is controlled in its position by controller 2 so that it can be moved in an arbitrary direction with a precision of 0.1 $\mu m$ or less. In addition, it can be rotated around an axis perpendicular to the sheet of the drawing with a precision of $\simeq 1$ m rad. A positioning and angular control signal from controller 2 and an output signal from detector 6 are processed by signal processor 7, and then supplied to an output unit 8.

Examples of the optical system to be used in this embodiment are shown in FIGS. 2 to 6. These optical elements have low aberrations (which means that light can be focused in a very small region) and excellent reflection coefficients as compared with the transmission and diffraction efficiency of the zone plate.

For example, reflective mirror 11 shown in FIG. 2 has a compound surface consisting of parts of an ellipsoid 9 and a hyperboloid 10. This is an optical system called Wolter type optics. The combination of the ellipsoid and hyperboloid can reduce the aberration to about 1/1000 as compared with the conventional light converging system using Bragg reflection on a single crystal surface. Moreover, the reflection coefficient of the compound surface can easily be increased to several tens of %, which is much higher than the transmission and diffraction efficiency of zone plates.

Wolter type optics other than that shown in FIG. 2, which are formed by the combination of an ellipsoid, a hyperboloid and a paraboloid, can be used in this invention. The actual optics consists of an axisymmetric surface (for example, compound mirrors 14, 15 FIG. 5) formed by rotating mirror 11 around the x-axis, or a portion of an axisymmetric surface (for example, compound mirror 17 in FIG. 6).

Figure 4:
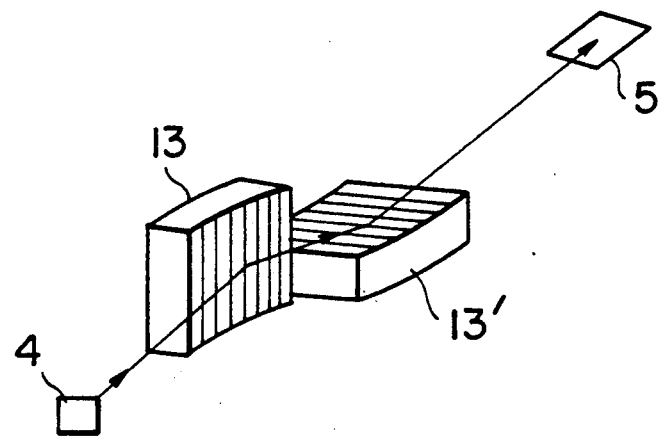

In addition to the Wolter type optics, Karkpatric-Baez optics (FIG. 3) has small aberrations with a high x-ray reflection coefficient. The aberration can be further decreased by forming grooves with a changing interval on surfaces of mirrors 13, 13' (FIG. 4). Thought not shown, tandem type optics using the compound surface can be utilized. Using the optical systems mentioned above, light ranging from a soft x-ray region to a vacuum ultraviolet region can be focused on a surface area below 1 $\mu m \phi$ with a high light collecting efficiency.

Figure 5:
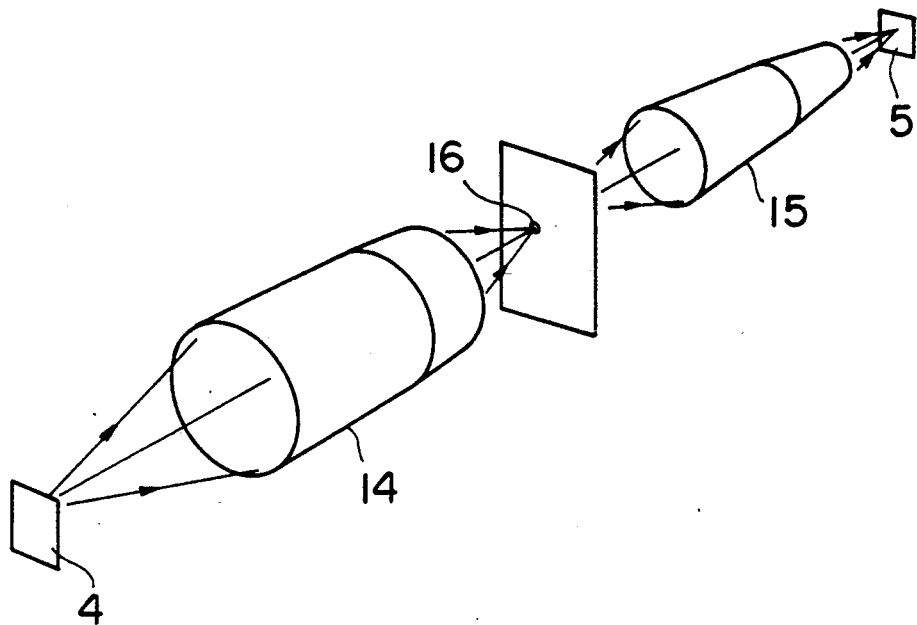
Figure 6:
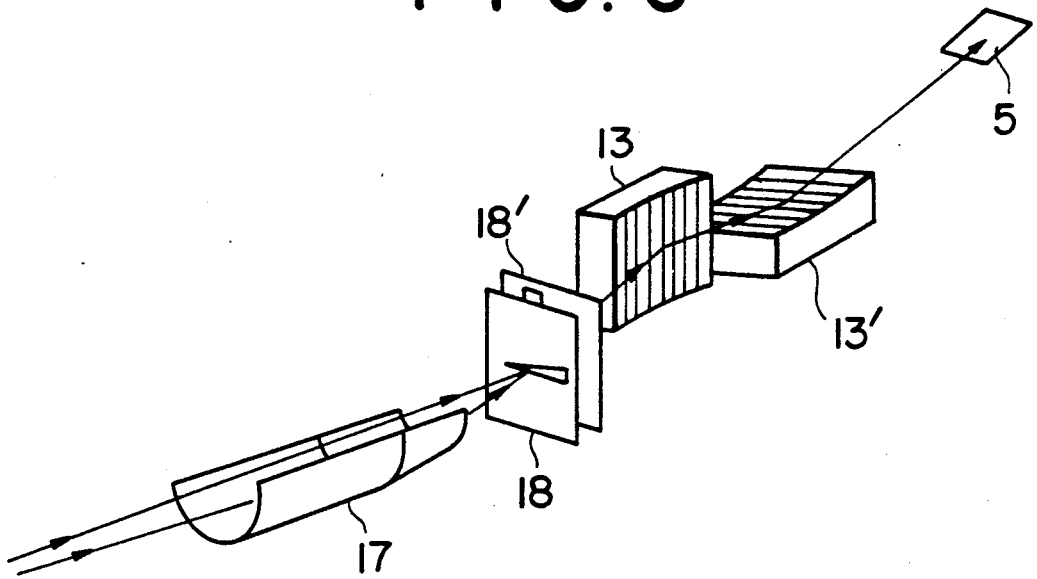

A combination of the above-mentioned optics are used in order to focus the light on a smaller area. FIG. 5 shows one example thereof. In FIG. 5, the light is focused on pinhole 16 by compound mirror 14. The light is shaped on pinhole 16, and then more sharply focused on sample 5 by compound mirror 15. FIG. 6 shows variable slits 18, 18' instead of pinhole 16. Slits 18, 18' enable the spot size of the light on sample 5 to be changed.

In FIGS. 5 and 6, compound mirrors 14, 15, 17 or part of mirrors 13, 13' can be replaced by zone plates. When all the optical elements are replaced by zone plates the amount of light incident to sample 5 is extremely reduced due to the low transmission and diffraction efficiency of the zone plates, so sample 5 cannot be analyzed. However, if the zone plate is used in part thereof, a decrease in the amount of incident light is small as compared with the case of replacing the optical elements with zone plates.

In this embodiment, by using optical system 3, it is possible to analyze a small surface area with a diameter of 1 $\mu m$ or less (here, the area size is defined as the full width at half maximum (FWHM) of the beam intensity profile on the sample surface) while maintaining a large signal intensity and sensitivity. Moreover, it is possible to obtain a magnified image of the surface of sample 5, and to find particular atomic species and chemical bonds within a very small region. Also, by moving sample table 1 to change the light spot position, it is possible to find the distribution of particular atomic species and chemical bonds on the surface of sample 5. Furthermore, since the incident angle of light to the surface of sample 5 can be adjusted, it is possible to find the distribution of atomic species or the like in the depth direction.

EMBODIMENT 2

Figure 7:
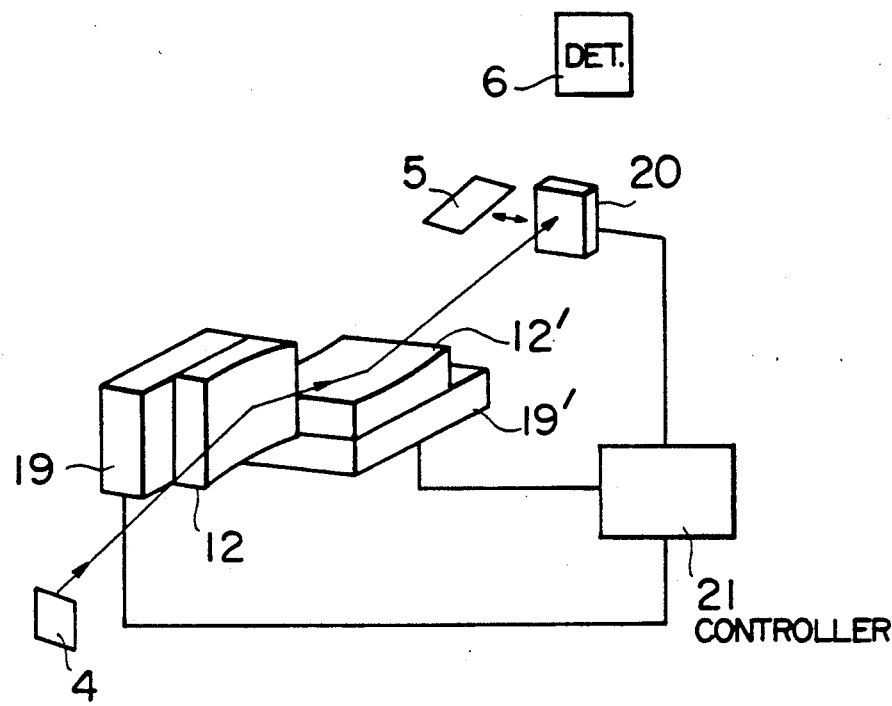
FIGS. 7 to 16 are arrangements of other embodiments of this invention.

Upon analyzing, the probe beam diameter may deviate from an expected value. In such a case, it is necessary to adjust the optics, monitoring the beam diameter and the beam intensity. FIG. 7 shows another embodiment of the invention in which adjustable optics are used. Mirrors 12, 12' and fine adjustment mechanisms 19, 19' are shown in FIG. 7. The beam spot position and beam diameter are measured with beam monitor 20 and the measured result is fed back to controller 21. In response to this fed-back signal, controller 21 supplies a control signal to fine adjustment mechanisms 19, 19', thus adjusting the position of mirrors 12, 12', the angle thereof to the light axis, and the distance therefrom to light source 4 and to sample 5. It is preferable to use piezoelectric devices for position and angle fine adjustment. In addition, if the thickness of mirrors 12, 12' is thin, it is possible to change the curvature of mirrors 12, 12' and to increase the freedom of beam adjustment.

EMBODIMENT 3

Figure 8:
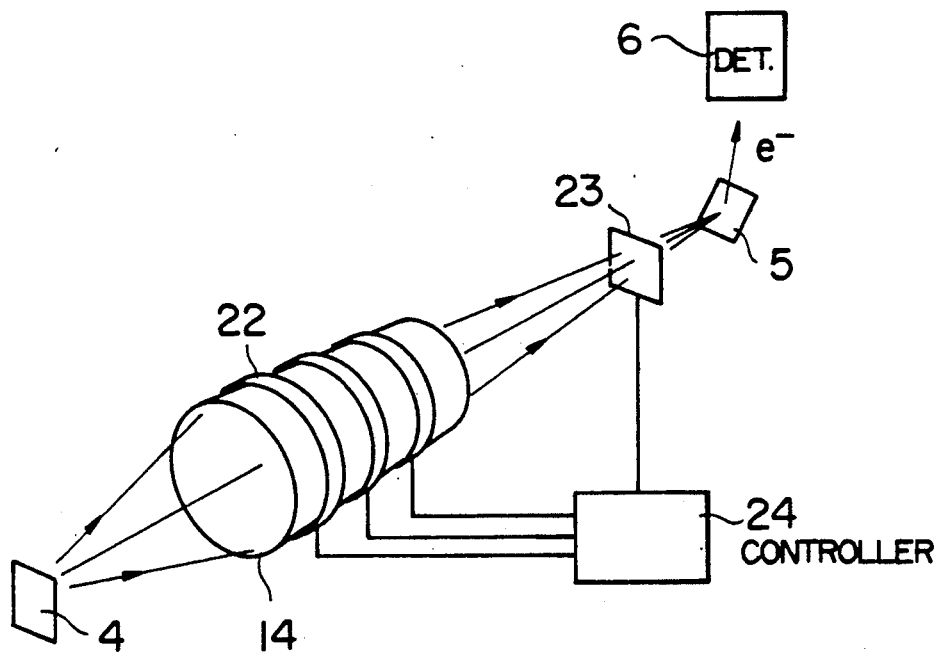

FIG. 8 shows still another embodiment of this invention in which the beam adjustment is possible. In FIG. 8, beam monitor 23 is inserted between compound mirror 14 and sample 5 so that the beam adjustment is possible upon analysis. Fine adjustment mechanism 22 uses local heating. Heating a part of compound mirror 14 enables the heated part to be changed in its curvature, thus changing the beam diameter on the surface of sample 5. In this embodiment, the fine adjustment mechanisms for position and angle may of course be provided.

The beam monitor and fine adjustment mechanisms shown in FIGS. 7 and 8 will be provided for each optical element. As the number of the optical elements used is increased, the number of the beam monitors and fine adjustment mechanisms may be increased if necessary.

EMBODIMENT 4

Figure 9:
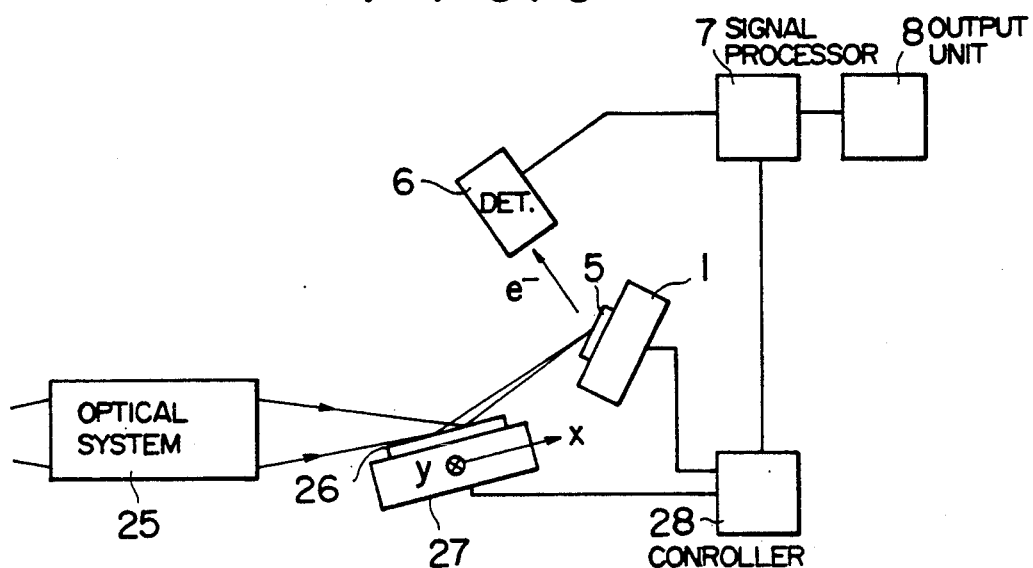
Figure 10:
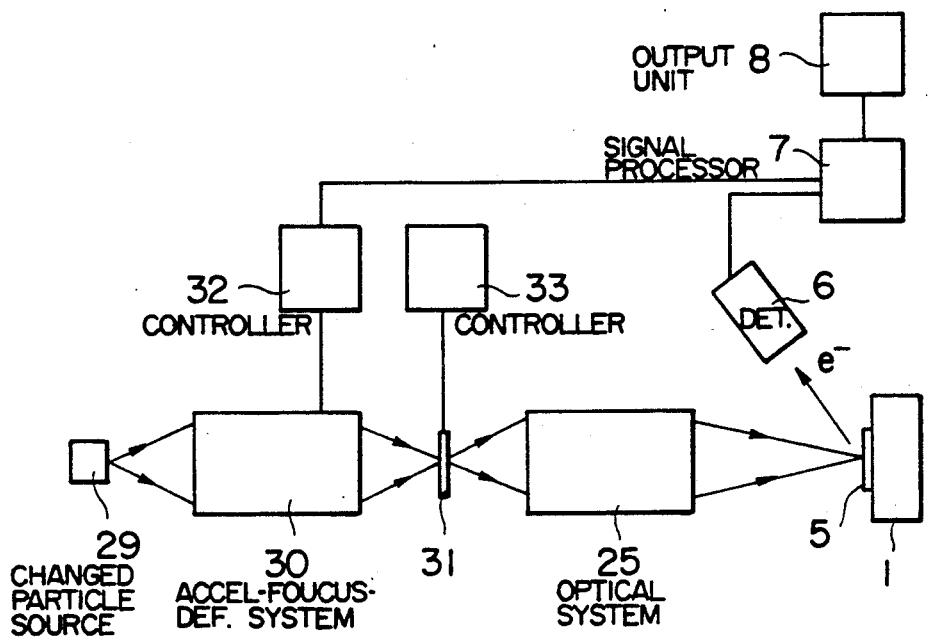
Figure 11:
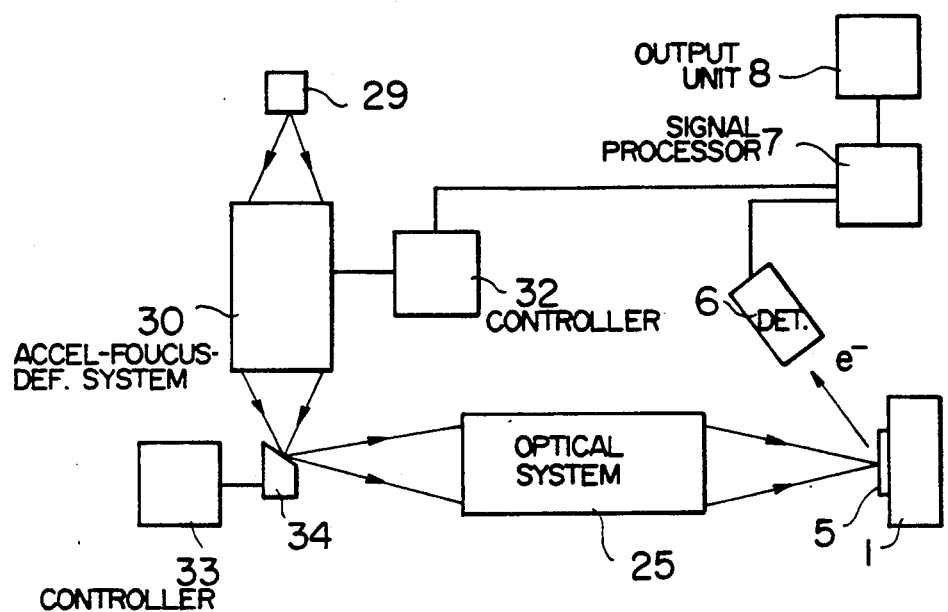

In the embodiments shown in FIGS. 1, 7 and 8, the distribution of elements and so on is measured by moving sample table 1. This can also be achieved by scanning the light beam on the surface of sample 5 (in general, movement of the incident beam offers a higher scanning speed and is more easily achieved than movement of the sample). Embodiments of this system are shown in FIGS. 9 to 11. In FIG. 9, mirror 26 for light beam scanning is interposed between optical system 25 and sample 5. Optical system 25 is optics with the fine adjustment mechanism mentioned in the previous embodiment. The light from the light source is focused by optical system 25 and reflected by mirror 26 onto the surface of sample 5. Mirror 26 is positioned on control table 27, which is controlled by controller 28. Control table 27 can be rotated around the x and y axes so that mirror 26 is slightly rotated by control table 27, thereby scanning the light beam.

EMBODIMENT 5

While in FIG. 9 the light beam is deflected and scanned in the course of being focused, the light source may be moved for scanning the light beam on the surface of the sample. FIG. 10 shows one example thereof. In FIG. 10, the charged particles from charged particle source 29 are accelerated, focused and deflected by acceleration-focusing-deflection system 30, and irradiate a surface of target 31. The irradiation of the charged particles cause the emission of light ranging from the soft x-ray region to the vacuum ultraviolet region. This light is focused by optical system 25 onto the surface of sample 5. In this case, when the charged particle beam is deflected by controller 32, the point where the emission of light occurs is changed on target 31, enabling the scanning of light on the surface of sample 5. Controller 33 is a controller for cooling target 31. In this embodiment, target 31 is a thin film, and the probe beam is taken out from the opposite side to the side on which the charged particles irradiate target 31.

EMBODIMENT 6

In order to reduce heat damage to the target material, it is better to use a block material for the target. FIG. 11 shows an example thereof. Target 34 is made of a block material, and the probe beam is taken out from the same side as the charged particle irradiated side of target 34. The action and operation of the other portions are the same as those in the embodiment shown in FIG. 10.

Instead of the charged particle beams, intense light such as a laser beam may also be used for generating the light on target 31 or 34. The embodiments shown in FIGS. 1 to 11 can make chemical state analysis in the region of 1 $\mu m\phi$ or less.

EMBODIMENT 7

Figure 12:
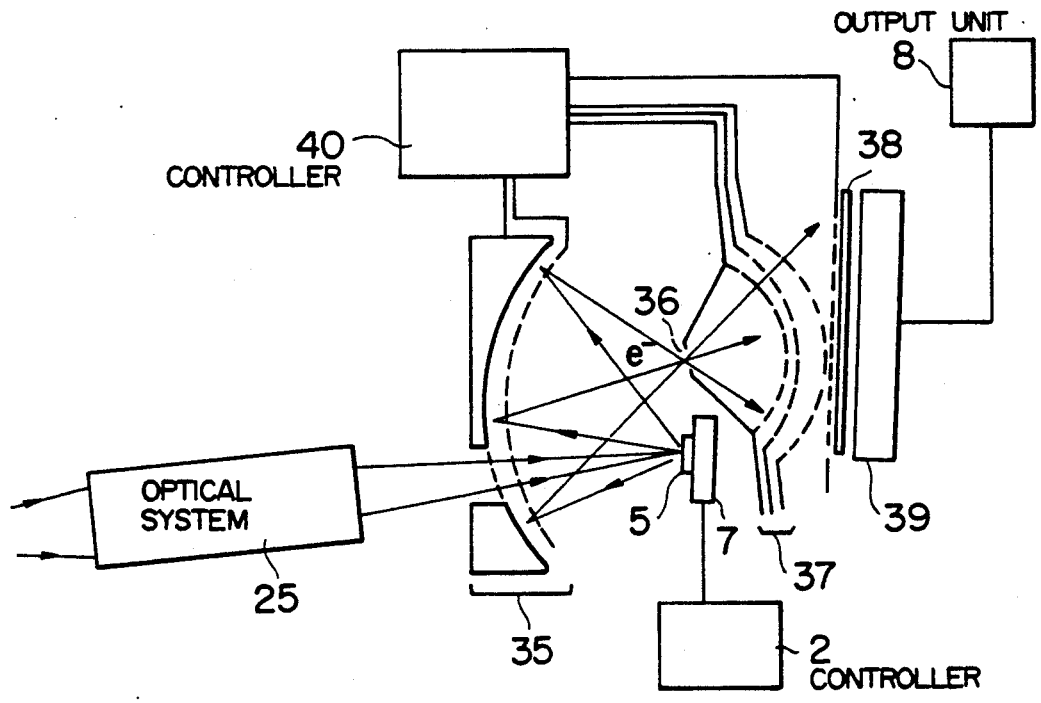

In the above described embodiments, the detector 6 may be of any type as long as it enables energies of emitted photoelectrons to be analyzed. For example, it may be a CMA (cylindrical mirror type analyzer), a retarding field analyzer, or a hemispherical deflection analyzer which is used in LEED. The detector shown in FIG. 12 is a display type (projection type) energy analyzer (D. E. Eastman et al., Nucl. Instrum. Methods, 172, 327-336 (1980)). This type of analyzer has the feature that the electron collecting angle is large. The photoelectrons emitted from a surface of sample 5 undergo energy measurement in low-pass filter 35 and high-pass filter 37, and then impinge on phosphor plate 38. Aperture 36 is provided between low-pass filter 35 and high-pass filter 37. Phosphor plate 38 emits fluorescent light, which is detected by using two-dimensional light detector 39. The detectors described above can be used in any embodiments of this invention.

EMBODIMENT 8

For the sample very susceptible to damage, the light source is designed to generate a light pulse. Alternatively, it is effective to modulate the light beam by use of electrical or mechanical means. The pulsed light source may be a plasma x-ray source, or the light source where pulsed charged particle beams are used for the bombardment of targets 31, 34 as shown in FIGS. 10, 11.

EMBODIMENT 9

Figure 13:
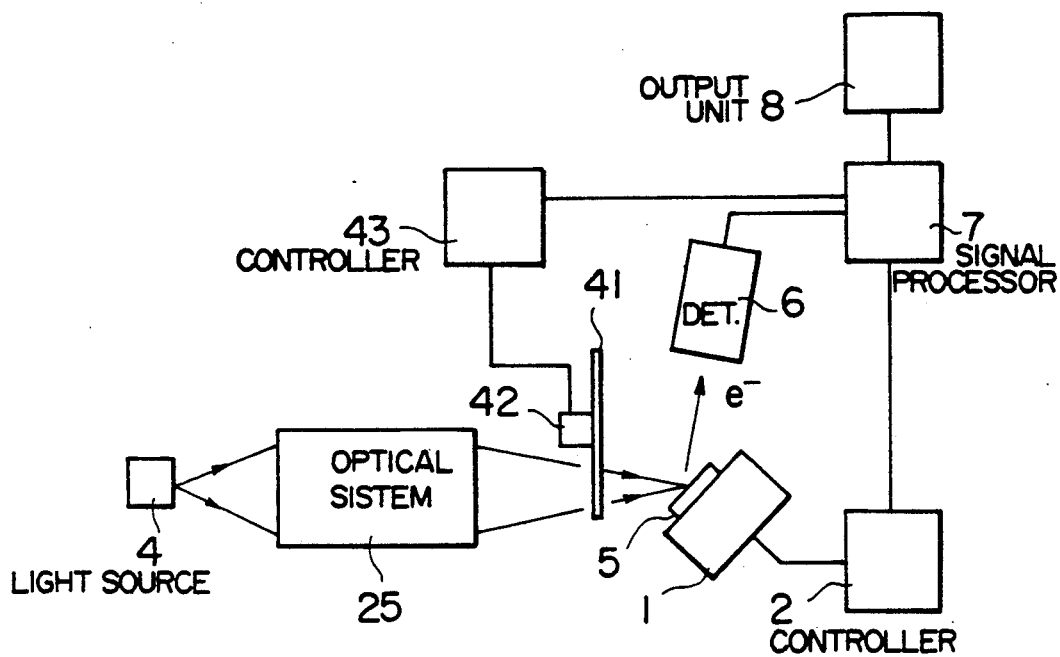

FIG. 13 shows an example of modulating the light beam. In FIG. 13, the light beam from optical system 25 is passed through chopper 41 and focused on sample 5. The chopping frequency is adjusted by controlling chopper drive motor 42 with controller 43. The signal associated with the chopping is supplied to signal processor 7 as a reference signal. The chopping system shown in this example may be replaced by another chopping system using a high frequency vibrator or the like. According to this embodiment, a sample susceptible to damage may be analyzed, since light intermittently irradiates the sample surface.

EMBODIMENT 10

Figure 14:
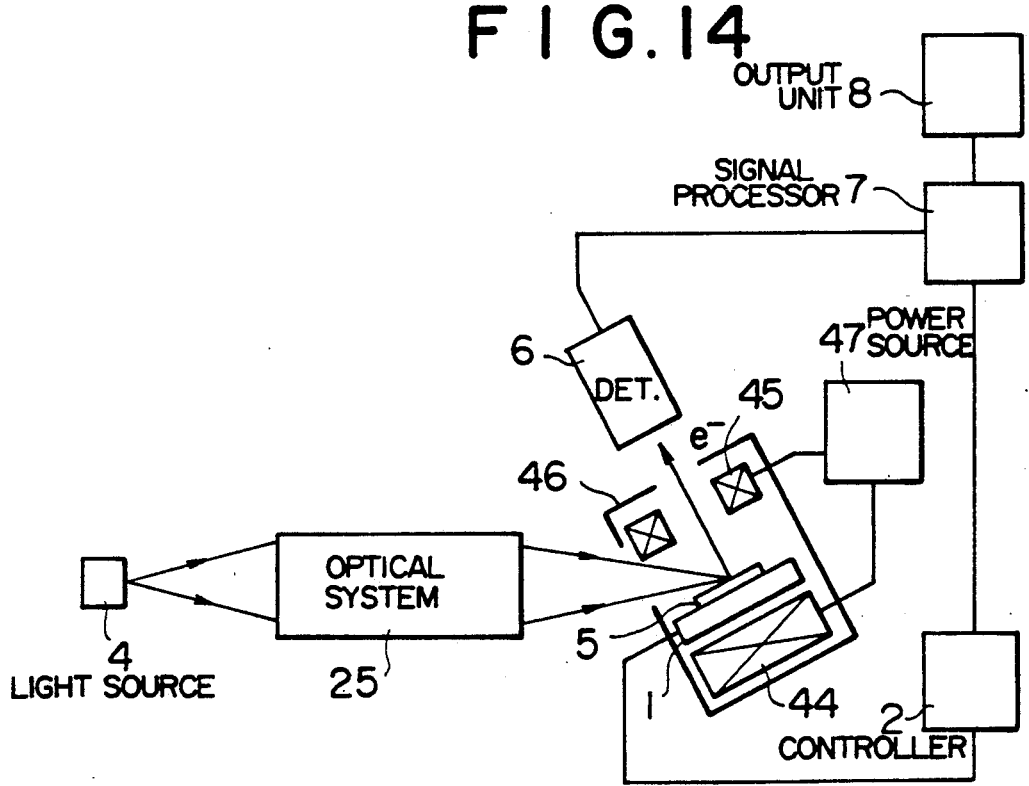

An embodiment shown in FIG. 14 is effective to analyze the bottom surface of a deep groove or the like. As shown in FIG. 14, coils 44 and 45 are located below and above sample 5. Coils 44 and 45 can produce strong magnetic field ($>1$ T) near the surface of sample 5 when they are supplied with electrical power from power supply 47. These coils enable detector 6 to catch more electrons from the deep groove bottom surface or the like. As the magnetic flux density near the surface of sample 5 is increased, a groove with a larger aspect ratio can be analyzed. Magnetic shield 46 is also shown in FIG. 14. Although this embodiment employs a static magnetic field, a pulsed magnetic field may be used for greater magnetic flux density near the surface of sample 5.

EMBODIMENT 11

Figure 15:
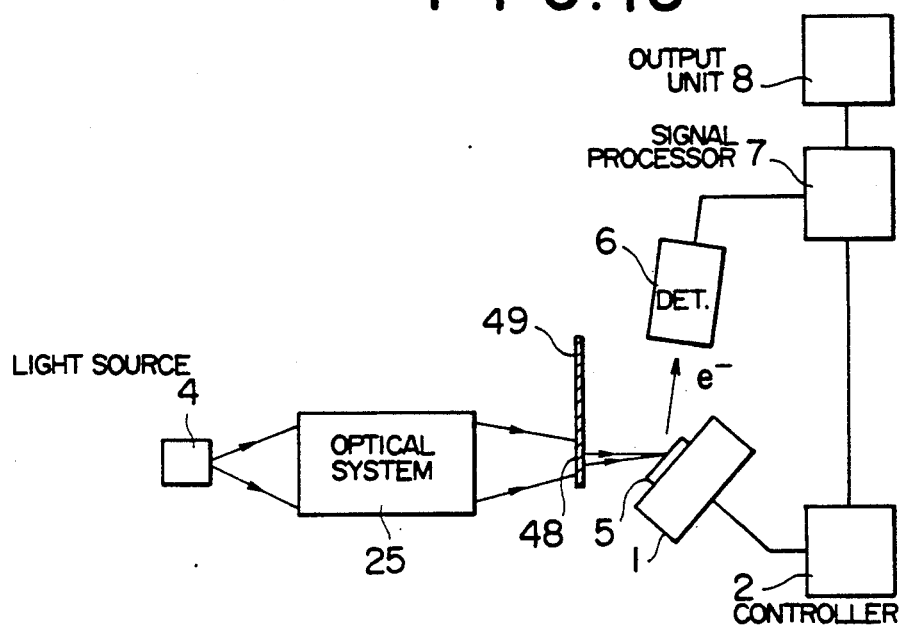

Another embodiment will be described which uses a combination of the focused light in soft x-ray to vacuum ultraviolet region and another system. FIG. 15 shows an embodiment which is a combination of optical system 25 and pinhole 48 for focusing. In this embodiment, the light beam from optical system 25 is blocked by shielding plate 49. Only the light passing through pinhole 48 located on shielding plate 49 reaches the surface of sample 5. In this embodiment, optical system 25 is used as a condenser system for increasing the light intensity (density). The lateral resolution of this system is determined by the size of pinhole 48 and the distance between pinhole 48 and sample 5. If the wavelength of light to be used is much shorter than the diameter of pinhole 48 the resolution of 1 $\mu m$ or less can be easily obtained.

EMBODIMENT 12

Figure 16:
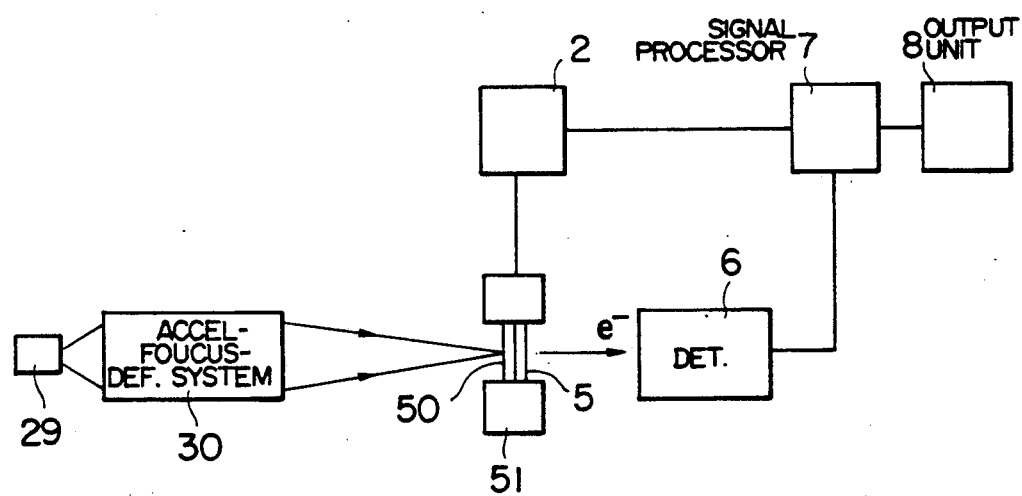

Sample 5 is a thin film (one $\mu m$ or less thick) in an embodiment shown in FIG. 16. In this embodiment, no light focusing optics is used, but from the viewpoint of chemical state analysis of a very small region, the same effect as in the embodiments mentioned above can be achieved by use of acceleration-focusing-deflection system 30. The charged particles from charged particle source 29 are focused on target 50 which is set on sample table 51 to be overlapped on sample 5. As described previously, it is possible to reduce the beam diameter to 0.01 $\mu m$ or less when the particle energy is several keV to several tens of keV. If the thickness of target 50 is one $\mu m$ or less, part of the light generated in target 50 by the irradiation of charged particles can pass through target 50 and reach sample 5. Thus, photoelectrons are produced in sample 5 and on the surface thereof. Since the photoelectrons cannot escape from a depth deeper than several tens of Å, the photoelectrons which can reach detector 6 are those produced near the surface on the side of detector 6. If the diameter of the charged particle beam incident to target 50 is sufficiently small (smaller than 1 $\mu m$), the surface analysis is possible in the surface region on the same order of size as the beam diameter.

Various different embodiments of this invention have been given above. Such embodiment as a combination of a plurality of these embodiments is of course included in this invention.

In the embodiments mentioned above, the particles emitted from the surface of sample 5 are electrons. When light the soft x-ray region to the vacuum ultraviolet region (particularly, the soft x-ray region) irradiates the surface of sample 5, light (other than electrons) is sometimes emitted. Chemical state information about atomic species and chemical bonds could be obtained from analyzing this light. Thus, the emitted light instead of the electrons may be observed. In this case, detector 6 is replaced by an energy dispersion type optical detector or by a spectrometer and an appropriate optical detector. This light detection or simultaneous detection of electrons and light can also be included in this invention.

Light source 4 is required to be monochromatic from the viewpoint of energy analysis. As long as light source 4 is monochromatized, it may be an arbitrary soft x-ray or vacuum ultraviolet light source. For example, it can include a charged particle bombardment type x-ray source using various target materials, a laser irradiation type x-ray source, and a vacuum ultraviolet light source using an intense line spectrum of rare gas. Also, synchrotron radiation can be used. If these light sources are not sufficiently monochromatic a spectrometer is used to obtain more highly monochromatic light from light source 4.

According to this invention, as described in detail, since light in the soft x-ray region to the vacuum ultraviolet region can be focused on the sample surface by using an optical system with small aberrations and a high collecting efficiency of light, it is possible to obtain chemical state information about a very small area, particularly with a diameter of 1 $\mu$m or less. As a result, it is possible to analyze residual contaminants on the surface of semiconductor circuit devices. Also, characterization of the surface of thin films or the like which are made of various different materials and analysis of non-uniform reaction on various surfaces become possible. Moreover, in the field of biological engineering or the like, it is possible to analyze atomic species and chemical structure of molecules.

We claim:

1. A surface analysis method for analyzing energies of particles which are emitted from a sample surface by irradiating said sample surface with light having wavelengths ranging from a soft x-ray region to a vacuum ultraviolet region through an optical system including a reflective optical element, wherein a beam diameter of said light on said sample surface is 1 $\mu$m or less in terms of full width at half maximum of a beam intensity profile on said sample surface.

2. A surface analysis method according to claim 1, wherein said particles are electrons, photons, or both.

3. A surface analysis method according to claim 1, wherein said particles are photoelectrons.

4. A surface analysis method according to claim 1, wherein said reflective optical element is a combination of at least two of an axisymmetric ellipsoid mirror, an axisymmetric hyperboloid mirror, and an axisymmetric paraboloid mirror, or a combination of portions of at least two of said axisymmetric mirrors.

5. A surface analysis method according to claim 4, wherein said optical system focuses the light on said sample surface, a shape of said focused light being modified by a pinhole or a slit.

6. A surface analysis method according to claim 4, wherein said optical system further includes a pinhole of a slit placed before said sample surface.

7. A surface analysis method according to claim 4, wherein said sample is moved relative to an optical axis of said optical system to measure a distribution on said sample surface.

8. A surface analysis method according to claim 4, wherein a distribution on said sample surface is measured by deflecting the light through the optical system to scan the light on said sample surface.

9. A surface analysis method according to claim 4, wherein a distribution on said sample surface is measured by changing a position of a light source generating said light to scan the light on said sample surface.

10. A surface analysis method according to claim 9, wherein said light source is a target irradiated with a particle beam, and wherein the position of said light source is changed by changing an irradiation position of the particle beam on the target.

11. A surface analysis method according to claim 10, wherein an intensity of said particle beam is modulated.

12. A surface analysis method according to claim 4, wherein while one or more of a position, an intensity, and a diameter of the light on the sample surface is monitored, one or more of a position, an angle to an optical axis of said optical system, and a curvature of the reflective optical element is adjusted.

13. A surface analysis method according to claim 4, wherein while one or more of a position, an intensity, and a diameter of the light is monitored on the way to the sample surface, one or more of a position, an angle to an optical axis of said optical system, and a curvature of the reflective optical element is adjusted.

14. A surface analysis method according to claim 4, wherein said energies of said particles emitted from the sample surface are analyzed with a projection type energy analyzer.

15. A surface analysis method according to claim 4, wherein a magnetic field whose magnetic flux density is 1 T or more is produced near the sample surface.

16. A surface analysis method according to claim 4, wherein an intensity of said light on said sample surface is modulated.

17. A surface analysis method according to claim 1, wherein said optical system includes a plurality of cylindrical mirrors, a plurality of spherical mirrors, or a plurality of cylindrical mirrors having grooves formed on the surfaces of said mirrors.

18. A surface analysis method according to claim 1, wherein said optical system does not employ Bragg reflection.

19. A surface analysis method for analyzing energies of particles which are emitted from a sample surface by irradiating said sample surface with light having energies in the range of 6 eV to 2000 eV through an optical system including a reflective optical element, wherein a beam diameter of said light on said sample surface is 1 $\mu$m or less in terms of full width at half maximum of a beam intensity profile on said sample surface.

20. A surface analysis method for analyzing energies of particles which are emitted from a surface of a sample by irradiating said sample with light having wavelengths ranging from a soft x-ray region to a vacuum ultraviolet region, said light being generated by irradiating a rear surface of said sample or a surface of a substance disposed on a rear surface of said sample with a particle beam having a beam diameter of 1 $\mu$m or less in terms of full width at half maximum of a beam intensity profile on the rear surface of said sample or on the surface of said substance disposed on said rear surface of said sample.

21. A surface analysis method according to claim 3, wherein said particles emitted from said surface of said sample are electrons, photons, or both.

22. A surface analysis method according to claim 20, wherein said particles emitted from said surface of said sample are photoelectrons.

23. A surface analysis method according to claim 20, wherein a distribution on said surface of said sample is measured by changing an irradiation position of said particle beam on said rear surface of said sample or on said surface of said substance disposed on said rear surface of said sample.

24. A surface analysis apparatus comprising:
 means for emitting light having wavelengths ranging from a soft x-ray region to a vacuum ultraviolet region;
 an optical system including a reflective optical element for reducing a beam diameter of said light to 1 μm or less in terms of full width at half maximum of a beam intensity profile on said sample surface; and
 means for analyzing energies of particles emitted from said sample surface in response to said light.

25. A surface analysis apparatus according to claim 24, wherein said analyzing means analyzes energies of electrons, photons, or both.

26. A surface analysis apparatus according to claim 24, wherein said analyzing means analyzes energies of photoelectrons.

27. A surface analysis apparatus according to claim 23, wherein said reflective optical element is a combination of at least two of an axisymmetric ellipsoid mirror, an axisymmetric hyperboloid mirror, and an axisymmetric paraboloid mirror, or a combination of portions of at least two of said axisymmetric mirrors.

28. A surface analysis apparatus according to claim 27, wherein said optical system focuses the light on said sample, surface, a shape of said focused light being modified by a pinhole or a slit.

29. A surface analysis apparatus according to claim 27, wherein said optical system includes a pinhole or a slit placed before the sample surface.

30. A surface analysis apparatus according to claim 27, further comprising means for moving said sample.

31. A surface analysis apparatus according to claim 27, further comprising light deflection means for scanning the light on said sample surface.

32. A surface analysis apparatus according to claim 27, further comprising means for changing a position of a light source generating said light for scanning the light on said sample surface.

33. A surface analysis apparatus according to claim 32, wherein said light source is a target irradiated by a particle beam, and wherein said light source position changing means scans the particle beam on the target.

34. A surface analysis apparatus according to claim 33 further comprising modulating means is provided for modulating an intensity of said particle beam.

35. A surface analysis method according to claim 27, further comprising:
 monitor means for monitoring one or more of a position, an intensity, and a diameter of the light on the sample; and
 adjustment means responsive to said monitor means for adjusting one or more of a position, an angle to an optical axis of said optical system, and a curvature of the reflective optical element.

36. A surface analysis apparatus according to claim 27, further comprising:
 monitor means for monitoring a position, an intensity, and a diameter of the light on the way to said sample surface; and
 adjustment means responsive to said monitor means for adjusting one or more of a position, an angle to an optical axis of said optical system, and a curvature of the reflective optical element.

37. A surface analysis apparatus according to claim 27, wherein the means for analyzing energies of particles emitted from the sample surface is a projection type energy analyzer.

38. A surface analysis apparatus according to claim 27, further comprising magnetic field generating means for producing a magnetic field near the sample surface.

39. A surface analysis apparatus according to claim 27, further comprising modulating means for modulating an intensity of said light on said sample surface.

40. A surface analysis apparatus according to claim 7, wherein an adjustable heat source is provided near at least one of said axisymmetric ellipsoid mirror, said axisymmetric hyperboloid mirror, and said axisymmetric paraboloid mirror for adjusting a curvature of at least one of said axisymmetric ellipsoid mirror, said axisymmetric hyperboloid mirror, and said axisymmetric paraboloid mirror.

41. A surface analysis apparatus according to claim 24, wherein said optical system includes a plurality of cylindrical mirrors, a plurality of spherical mirrors, or a plurality of cylindrical mirrors having grooves formed on surfaces of said mirrors.

42. A surface analysis apparatus according to claim 24, wherein said optical system does not employ Bragg reflection.

43. A surface analysis apparatus comprising:
 means for emitting light having energies in the range of 6 eV to 2000 eV;
 an optical system including a reflective optical element for reducing a beam diameter of said light to 1 μm or less in terms of full width at half maximum of a beam intensity profile on said sample surface; and
 means for analyzing energies of particles emitted from said sample surface in response to said light.

44. A surface analysis apparatus comprising:
 means for irradiating a particle beam on a rear of a sample surface or on a surface of a substance disposed on a rear surface of a sample to generate light having wavelengths ranging from a soft x-ray region to a vacuum ultraviolet region;
 control means for reducing a beam diameter of said particle beam to 1 μm or less in terms of full width at half maximum of a beam intensity profile on the rear surface of said sample or on the surface of the substance disposed on said rear surface of said sample; and
 means for analyzing energies of particles emitted from said surface of said sample in response to said light.

45. A surface analysis apparatus according to claim 44, wherein said analyzing means analyzes energies of electrons, photons, or both.

46. A surface analysis apparatus according to claim 44, wherein said analyzing means analyzes energies of photoelectrons.

47. A surface analysis apparatus according to claim 44, further comprising means for scanning the particle beam on said rear surface of said sample or on said surface of said substance disposed on said rear surface of said sample.

48. A surface analysis method for analyzing energies or particles which are emitted from a sample surface when light having wavelengths ranging from a soft x-ray region to a vacuum ultraviolet region is focused on said sample surface using an optical system including a reflective optical element, wherein a resolution of analysis on the sample surface is 1 $\mu$m or less.

49. A surface analysis method for analyzing one or more of atomic species, composition, and chemical bonds on or near a sample surface by focusing light having wavelengths ranging from a soft x-ray region to a vacuum ultraviolet region on said sample surface using an optical system including a reflective optical element, wherein a resolution of analysis on the sample surface is 1 $\mu$m or less.

50. A surface analysis method for analyzing energies of electrons, light, or both which are emitted from a sample surface when light having wavelengths ranging from a soft x-ray region to a vacuum ultraviolet region is focused on said sample surface using an optical system including a reflective optical element, wherein a resolution of analysis on the sample surface is 1 $\mu$m or less.

51. A surface analysis method for analyzing energies of photoelectrons, Auger electrons, or both which are emitted from a sample surface when light having wavelengths ranging from a soft x-ray region to a vacuum ultraviolet region is focused on said sample surface using an optical system including a reflective optical element, wherein a resolution of analysis on the sample surface is 1 $\mu$m or less.

52. A surface analysis method for analyzing energies of particles which are emitted from a sample in response to light having wavelengths ranging from a soft x-ray region to a vacuum ultraviolet region, said light being generated by a particle beam having a controlled beam diameter which irradiates a rear surface of the sample or a surface of a substance disposed on a rear surface of the sample, wherein a resolution of analysis on the sample surface is 1 $\mu$m or less.

* * * * *